(12) United States Patent
Neiman (10) Patent No.: US 6,946,266 B2
(45) Date of Patent: Sep. 20, 2005

(54) GENE TRANSFER IN CHICKEN BURSAL STEM CELLS

(75) Inventor: Paul E. Neiman, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 280 days.

(21) Appl. No.: 10/025,199

(22) Filed: Dec. 18, 2001

(65) Prior Publication Data

US 2002/0114790 A1 Aug. 22, 2002

Related U.S. Application Data

(60) Provisional application No. 60/257,142, filed on Dec. 20, 2000.

(51) Int. Cl.$^7$ .......................... C12P 21/00; C12N 15/85
(52) U.S. Cl. .................... 435/69.7; 435/69.1; 435/455; 435/456; 800/4; 800/23
(58) Field of Search .................................. 435/455, 456, 435/69.1, 69.7; 800/4, 23

(56) References Cited

U.S. PATENT DOCUMENTS

| | | | |
|---|---|---|---|
| 5,470,726 A | 11/1995 | Miller et al. | ................. 435/465 |
| 5,766,945 A | 6/1998 | Miller | ..................... 435/235.1 |

OTHER PUBLICATIONS

Neiman et al. A retroviral myc gene induces preneplastic transformation of lymphocytes in a bursal transplanation assay. Proc Natl Acad Sci U S A. Jan. 1985;82(1):222–6.*
Thompson et al. The effect of alterations in myc gene expression on B cell development in the bursa of Fabricius. Cell. Nov. 6, 1987;51(3):371–81.*
Lee et al. Role of Nr13 in regulation of programmed cell death in the bursa of Fabricius. Genes Dev. Mar. 15, 1999;13(6):718–28.*
Database Swiss–Prot entry P06295.*
Burns et al., "Vesicular stomatis virus G glycoprotein pseudotyped retroviral vectors: concentration to very high titer and efficient gene transfer into mammalian and non-mammalian cells," *Proc. Nat'l Acad. Sci. USA*, 90:8033–8037, 1993

Eskola and Toivanen, "Effect of in Ovo treatment with cyclophosphamide on lymphoid system in chicken," *Cell Immunology*, 13:459–471, 1974.
Landau et al., "Packaging system for rapid production of murine leukemia virus vectors with variable tropism," *J. Virol.*, 66:5110–5113, 1992.
Lee et al., "Role of Nr13 in regulation of programmed cell death in the bursa of fabricius," *Genes & Development*, 13:718–728, 1999.
Miller et al., "Cloning of the celluar receptor for amphotropic murine retroviruses reveals homology to that for gibbon ape leukemia virus," *Proc. Nat'l Acad. Sci. USA*, 91:78–82, 1994.
Miller et al., "Construction and properties of retrovirus packaging cells based on gibbon ape leukemia virus," *J. Virol.*, 65(5):2220–2224, 1991.
Neiman et al., "Induction of apoptosis during normal and neoplastic B–cell development in the bursa of Fabricius," *Proc. Nat'l Acad. Sci. USA*, 88:5857–5861, 1991.
Thompson et al., "The effect of alterations in myc gene expression on B cell development in the Bursa of fabricius," *Cell*, 51:371–381, 1987.
Yee et al., "A general method for the generation of high–titer, pantropic retroviral vectors: highly efficient infection of primary heptocytes," *Proc. Nat'l Acad. Sci. USA*, 91:9564–9568, 1994.
Yom et al., "Genetic engineering of milk composition: modification of milk components in lactating transgenic animals," *Amer. J. Clin. Nutr.*, 58(suppl):299S–306S, 1993.

* cited by examiner

*Primary Examiner*—David Guzo
*Assistant Examiner*—Daniel M. Sullivan
(74) *Attorney, Agent, or Firm*—Fulbright & Jaworski (57) ABSTRACT

The invention relates to a method of expressing proteins in higher eukaryotes in vitro. In general, the invention sets forth a method of expressing exogenous proteins as fusion partners with the immunoglobulin molecules of avian species specifically chickens. The technology involves, in one embodiment, retroviral-mediated gene transfer and transplantation of stem cells from the Bursa of Fabricus in chickens.

27 Claims, 4 Drawing Sheets

GENE TRANSFER IN CHICKEN BURSAL STEM CELLS

This application claims benefit of priority from U.S. Provisional Application Ser. No. 60/257,142, filed on Dec. 20, 2000, the entire content of which is hereby incorporated by reference.

The government owns rights in the present invention pursuant to grant number CA20068 from the National Institutes of Health and support from the United States Department of Agriculture.

BACKGROUND OF THE INVENTION

A. Field of the Invention

The present invention relates generally to the field of protein expression. More particularly, it concerns the transfer and expression of a gene of interest by the immune cells of an avian.

B. Description of Related Art

There is a growing interest in the use of domesticated species in the production of recombinant proteins. Large scale and commercial production of recombinant proteins generally employs either bacterial or yeast systems. There are, nevertheless, drawbacks to these systems. Agricultural species have been proposed as suitable systems for use in the production of high quality recombinant proteins. Agricultural species are readily available and advances in molecular biology have allowed engineering of these species for the large scale production of proteins of interest.

There is a major and continuing effort to exploit germ-line transgenic technology for the production of useful heterologous proteins at commercial scales in the milk of transgenic animals. Success has been achieved for some proteins up to a level, in a few cases, of about a gram/liter of milk (Yom et al., 1993). However, the germline transgenic approach for large animals, for example dairy cattle, is still under development and requires a major investment of both time and money to create a transgenic breading stock for each protein.

The use of poultry species as a source of high quality, relatively inexpensive recombinant protein is largely unexplored. While it has been hypothesized that chicken B-cells may be useful in the production of recombinant proteins, to date this goal remains unrealized in any practical sense. The ability of avian B-cells to secrete large quantities of immunoglobulin into the egg yolk has, however, been commercially exploited.

Several companies now offer kits for the production and purification of chicken immunoglobulin, IgY. Immunized hens are used to produce high quantities of purified polyclonal IgY (equivalent to mammalian IgG). Fifty to eight milligram quantities of immunoglobulin IgY can be purified from individual egg yolks using simple, rapid and convenient methods. The ability to isolate and purify IgY has yet to be explored as a means of producing and purifying recombinant material.

The instant invention sets forth processes and methods for the production isolation and purification of high quality recombinant proteins from avian species, specifically from lymphoid cells.

SUMMARY OF THE INVENTION

The instant invention provides a means of expressing polypeptides in vivo in a higher eukaryotic species, specifically avians. In a preferred embodiment of the invention, a polypeptide is expressed by ablating a lymphoid cell population of the Bursa of Fabricius in an avian host embryo and then infusing transformed bursal stem cells into the embryo. The infused bursal stem cells have been transduced with a recombinant virus that contains a nucleic acid encoding the selected polypeptide. The infused stem cells repopulate the ablated bursa and give rise to the B-cells of the host. The selected polypeptide is ultimately expressed by the lymphoid cells of the avian host.

It is specifically contemplated that the lymphoid cells in the bursa of the avian host may be ablated in a number of ways. In a preferred embodiment, lymphoid cells are ablated with an alkylating agent, for example, cyclophosphamide. It is nevertheless further contemplated that the cells may be ablated by alternate means, including, for example radiation.

A number of avian species may be utilized as hosts for the expression system of the instant invention. It is particularly contemplated that avian species of commercial significance are applicable in the context of the invention with specific emphasis on chickens. In preferred embodiments of the invention, avian species for use in the invention are those strains inbred to share histocompatibility alleles to facilitate transplantation.

It is contemplated that the nucleic acid construct of the instant invention may be delivered to cells by a number of means known to one of skill in the art. In a preferred embodiment of the invention, the construct is delivered by a transducing virus, specifically a retrovirus.

The basic embodiment of the invention may be modified to facilitate more efficient protein production. In particular, the basic embodiment of the invention may be further characterized as comprising: obtaining bursal follicle cells from a first avian host following hatching and repopulating a second avian host embryo in which the lymphoid cells have been ablated.

It is recognized that the bursal stem cells undergo programmed elimination after hatching. In order to avoid bursal cells entering an apoptotic cycle, the nucleic acid construct of the invention, i.e., the transducing virus, may further encode an anti-poptotic factor capable of blocking this programmed elimination. In a preferred embodiment, the anti-apoptotic factor is NR-13 (Lee et al., 1999; which is incorporated herein by reference in its entirety).

A variety of proteins, polypeptides or proteins may be expressed in the context of the instant invention. Due to the ability of the system to facilitate the production of large quantities of a specific protein, it is particularly contemplated that the protein to be expressed will be a protein of commercial relevance. In a preferred embodiment, the expressed protein may be, for example, a peptide, a hormone, an immunomodulator, an enzyme, an antibody, a cell surface molecule, a DNA binding protein or a protein inhibitor, e.g., cyclin inhibitors.

It is envisioned that the construct encoding the selected polypeptide also comprises a nucleic acid encoding an immunoglobulin light chain. In an envisioned embodiment, the sequence encoding the selected polypeptide is ligated to a nucleic acid encoding a diversified immunoglobulin light chain. It is contemplated that the fusion between the selected polypeptide and immunoglobulin light chain encoding nucleic acids may be through a nucleic acid encoding cleavable peptide. In a preferred embodiment, the cleavable peptide sequence is an IgA hinge region. Where a cleavable sequence is present, it is specifically contemplated that the sequence may be cleaved. The cleaving of the cleavable sequence may further facilitate isolation and purification of the selected peptide.

The expression system disclosed herein facilitates the isolation and purification of large quantities of high quality protein. While it is contemplated that the fusion protein may be isolatable from the serum of a chicken, in a preferred embodiment of the invention the selected polypeptide is isolated from egg yolk.

Once isolated, the protein may be utilized in either a purified or an unpurified state. Where a purified protein is desired, a person of ordinary skill would be aware of a variety of methods of purification. In a preferred embodiment, purification is by ammonium sulfate precipitation. Where purification of the selected polypeptide is desired, it is contemplated that such purification will be up to 100-fold over the starting material or more. Polypeptide purification may be further characterized as reaching a point wherein the elected polypeptide is purified to be substantially free of other polypeptides. Although substantially free of other polypeptides should be construed based upon the application to which the polypeptide is to be applied, it is specifically contemplated that the selected polypeptide may be purified to 95% purity or up to and approaching homogeneity.

The host embryo for use in the instant invention may be used at a variety of stages of development from the time it is sufficiently differentiated until hatching. It is generally contemplated that this time frame is from day 10 to day 21. In a preferred embodiment the host embryo is 15 days old.

The embryonic bursal cells for use in the instant invention may be isolated from differentiation to hatching of the embryo. In as preferred embodiment, embryonic bursal cells are isolated from a 15 day-old embryo.

It is contemplated that the avian host embryo and the transplanted embryonic bursal cells are syngeneic. It is further contemplated that the avian host embryo is immunologically tolerant and the donor embryonic bursal cells expressing the polypeptide of interest are histocompatible.

The instant invention further provides a method of repopulating an avian host with transduced bursal cells. In a preferred embodiment, this method is carried out by providing a syngenic avian bursal stem cell, transducing the bursal stem cell with a first transducing virus that contains a nucleic acid encoding an apoptosis inhibitor and infusing an avian host with the transduced bursal stem cell. In a further embodiment, the transduction of the bursal stem cell is at a multiplicity of infection of greater than 1. It is further contemplated that the bursal stem cell may be transduced with a second transducing virus containing a nucleic acid encoding a selected polypeptide.

The instant invention further provides a method of repopulating an avian host with transduced bursal cells. In a preferred embodiment, this method is carried out by providing a histocompatible avian bursal stem cell, transducing into the bursal stem cell a vector containing a nucleic acid encoding a protein capable of blocking programmed stem cell elimination and infusing an avian host with the transduced bursal stem cells. In one embodiment, the transduction of the bursal stem cell is at a multiplicity of infection of greater than one. In one embodiment, the transduction of the bursal stem cell is transduced by co-culture with cells producing vector packaged in viral particles. It is further contemplated that the bursal stem cell may be transduced with a second transducing virus containing a nucleic acid encoding a selected polypeptide.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The instant invention relates to a means of expressing and purifying recombinant proteins from avian species, particularly chickens. The method involves the engineering of avian lymphoid cells to produce a recombinant protein. In brief, an avian host embryo's Bursa of Fabricus is ablated. The Bursa is then reconstituted with heterologous, modified bursal stem cells. At maturation, the B cells, which are the progeny of the engineered bursal stem cells express a fusion construct comprising the selected polypeptide.

The instant invention sets forth constructs, which may be useful in transducing lymphoid cells. A person of ordinary skill would nevertheless be aware of alternate constructs that would be equally applicable in the context of carrying out the claimed processes and methods. In an envisioned embodiment, the nucleotide sequence of a protein to be expressed is inserted into an expressing construct proximal to a avian diversified immunoglobulin light chain gene. The desired sequence is inserted such that, upon expression, the desired protein is fused to the carboxyl terminus of the immunoglobulin light chain. Upon assembly of the immunoglobulin molecule in vivo, the expressed fusion protein is located in the hinge region of the immunoglobulin molecule. Within one embodiment, a linker sequence between the expressed protein and the light chain molecule contains a cleavage site that facilitates the purification of the expressed protein.

Figure 1:
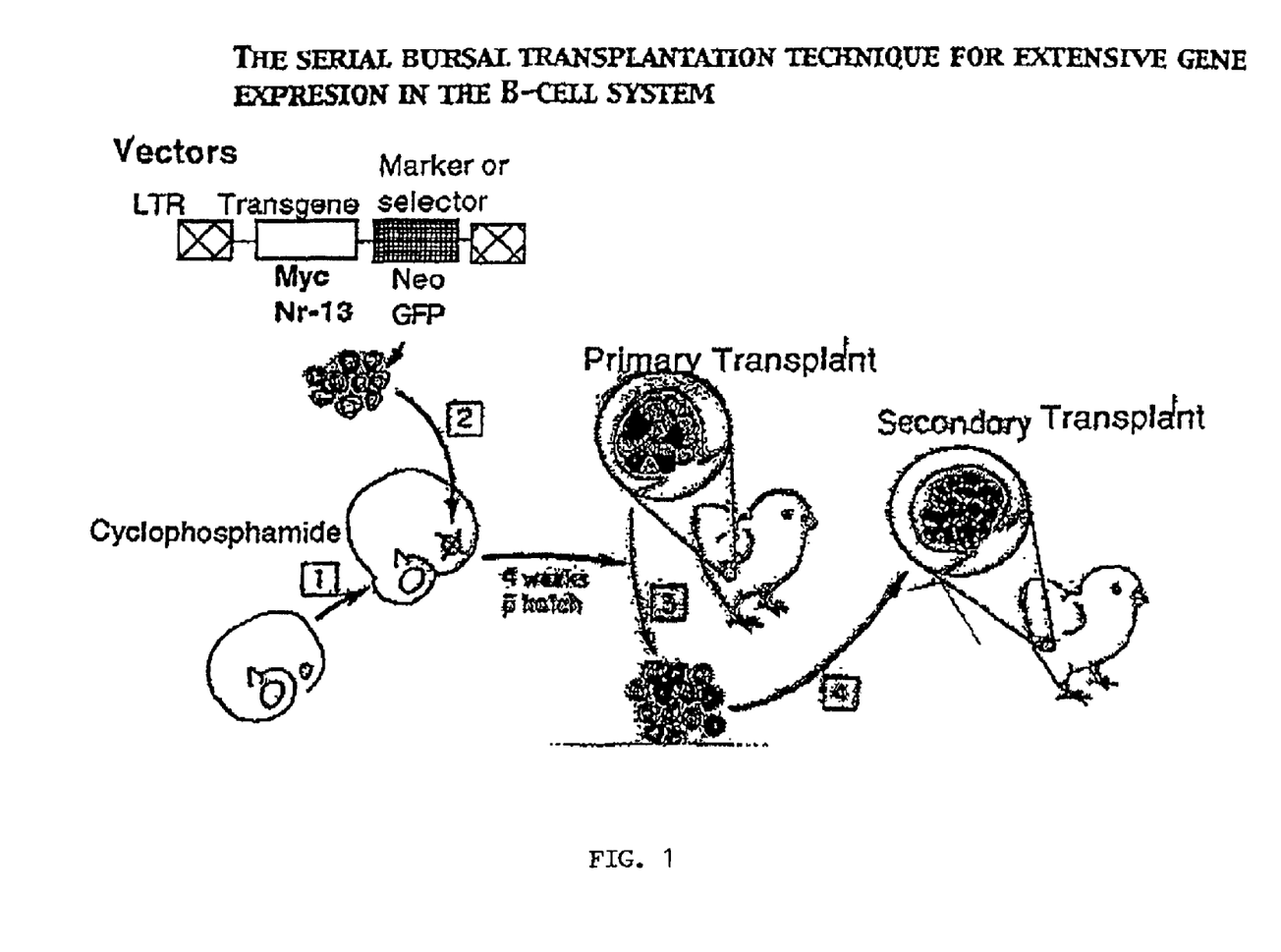
FIG. 1: Shows an exemplary serial transplantation method.

Once embryonic bursal cells are transduced with the described construct, a stepwise process facilitates the proper reconstitution of an ablated bursa with transformed cells. Within one example, a basic process of preparing chickens for and reconstituting the Bursa of Fabricus with transformed bursal cells is as follows (FIG. 1):

Step 1: ABLATION—The lymphoid population of recipient embryonic bursas are selectively ablated by treatment, for example, between 18 days of embryogenesis and day of hatch with the alkylating agent cyclophosphamide (Eskola et al., 1974)

Step 2: REPOPULATION—Embryonic bursal cell populations, e.g., from 15-day syngeneic donors, are transduced with a gene of interest and the Nr-13 gene and infused intravenously into recipients. Stem cells migrate to and repopulate ablated follicles.

Step 3: HARVESTING—Follicle cells harvested four weeks after hatching contain a mixed population in which the only cells capable of transplantation are stem cells. The anti-apoptotic Nr-13 gene is used because it also blocks stem cell elimination without causing transformation (Lee et al., 1999)

Step 4: PRODUCTION—NR-13 preserved stem cells are used to repopulate secondary cyclophosphamide treated recipients. In this case only gene-modified B-cells for transplant are produced. Metastatic lymphomas are produced by maintaining either primary (step 3) or secondary (step 4) reconstituted chicks for an additional 4 or more weeks.

In an embodiment of the invention, to enrich for cells capable of expressing the selected polypeptide, the follicle cells from the first host may be harvested and used to reconstitute the bursa of a second host embryo in which the native bursal stem cells have been ablated. In this embodiment, the selected polypeptide is expressed by the mature lymphoid cells of the second host.

Expressed protein may be isolated either from the primary or secondary recipient itself or from eggs produced by the either primary or secondary recipient. The protein or fusion protein may then be isolated and purified. In the context of the above described embodiment, the linking of the desired protein to an immunoglobulin molecule enhances the ability to isolate and purify the protein.

Avian immunoglobulin is transported into the yolk of the egg by the Fc receptor. This feature of avian Ig establishes eggs as an excellent source of immunoglobulin for isolation and purification. The egg yolk is readily obtainable, and isolation and purification methods are well known in the art. In brief, highly purified Ig-fusion proteins of greater than 90% may be obtained by aqueous extraction of yolk proteins, ammonium sulfate precipitation and chromatography. The Ig fusion protein may then be eluted from the column and the fusion partners cleaved. In an alternate embodiment, the desired protein may be cleaved directly from the bound Ig and eluted or treated with a protease such as, for example, IgA protease. Inclusion of an additional affinity label facilitates further purification of the expressed protein.

The instant invention facilitates the production of large quantities of high quality protein in a readily available eukaryotic species. The expression system has the added benefits that protein may be expressed into a readily accessible locale and attached to a fusion partner that allows for rapid and efficient purification.

A. Avian Immunology

The entire B-cell compartment of the avian immune system is composed of the progeny of stem cells of the follicles of the bursa of Fabricius. In chickens, the bursa of Fabricius is a developmentally regulated lymphoid organ essential for normal B-cell development. The features of bursal structure and physiology relevant to this discussion have been reviewed (Weill et al., 1987). Briefly, the bursa is composed of about $10^4$ repeating structural units called bursal follicles. The follicles contain about $10^4$ surface immunoglobulin (IgM) positive lymphocytes distributed either within a basement membrane-enclosed medulla containing a gut-derived epithelium, or in a cortex outside the basement membrane.

The collection of follicles develops within the folds of a diverticulum off of the cloaca beginning about day 10 of embryogenesis, and persists until bursal involution about three to four months after hatching. Based upon ablation studies two essential functions of the bursa are expansion of the B-cell mass and diversification of Ig genes (Jalkanen et al., 1984). In chickens, bursal-dependent preimmune diversification of the single functional light chain gene (IgL) proceeds by a gene conversion mechanism involving sequence donation from variable (V) region pseudogenes to a single functional V region (Reynaud et al., 1985) in a rearranged IgL allele which has undergone a V-J joining event (Thompson et al., 1987). Ig heavy-chain gene (IgH) preimmune diversification employs the same mechanism (Reynaud et al., 1989). All bursal lymphocytes undergo the same initial V region rearrangements making it possible for conversion-mediated sequence diversification of V regions to be monitored in whole bursal populations by simple restriction endonuclease digestion/Southern blot hybridization technology (Reynaud et al., 1985; Thompson et al. 1987).

The embryonic bursa contains a developmentally regulated compartment of transplantable bursal stem cells which disappears a few weeks after hatching (Eskola et al., 1974; Toivanen et al., 1973). This bursal stem cell compartment appears to be the target population for neoplastic change. An initiating event in this process is deregulation of expression of the c-myc protooncogene, for example as occurs after nearby integration of an avian leukosis virus (ALV) (Hayward et al., 1981). The resulting constitutive, high level myc expression appears to block differentiation and promote proliferation of bursal stem cells, so that bursal follicles become filled with a monomorphic population of pyroninophillic lymphoblasts producing a lesion called a transformed follicle (TF) (Cooper et al., 1960; Neiman et al., 1980; Baba et al., 1985).

TF cells grow only within and maintain the architecture of bursal follicles. They retain cardinal properties of bursal stem cells including the ability to reconstitute bursal follicles (as TF) in transplantation experiments and to diversify immunoglobulin genes by conversion at a rate similar to that of normal embryonic bursal cells (Thompson et al., 1987). They are abnormal, however, in persisting indefinitely into post-hatching life. They are also preneoplastic giving rise to invasive, metastasizing lymphomas. Natural or experimental infection of susceptible chickens with ALV either during embryonic life or a short period after hatching will induce small numbers of TF and derivative tumors over a period of three to six months (Cooper et al., 1960; Neiman et al., 1980; Baba et al., 1985).

Normally, B-cell precursors migrating to the bursa during embryogenesis carry out standard V-D-J rearrangements of light and heavy chain Ig genes (McCormack et al., 1989). Although the usual errors occur during recombination only cells which produce germ line, non-diversified Ig molecules on their cell surfaces initially populate embryonic bursal follicles. As mentioned above, diversification of Ig light and heavy chain V region genes then occurs by gene conversion followed by migration of B-cells with diversified surface Ig from the bursa to peripheral lymphoid organs. It seems rational to hypothesize, therefore, that the germ-line Ig receptors on cell surface are required for B-cell growth in the bursa and that diversification may change signaling through these receptors leading to migration out of the bursa. In addition it is known that there is a high level of spontaneous cell death in bursal follicles after hatching (Thompson et al., 1987). Although the reason for this phenomenon is unknown it seems reasonable to propose that signaling for these cell death events proceeds through Ig receptors and is modified by diversification of these surface molecules. The instant invention provides for the transfer of a construct encoding a light chain/fusion protein construct into bursal stem cells. In a preferred embodiment, retroviral vectors allow for the random integratation in the host cell genome so that these highly expressed transgenes are not located normally in cis with the cluster of V-region pseudogenes on which conversion-mediated Ig gene diversification depends (Reynaud et al., 1985; Thompson et al., 1987; Reynaud et al., 1989). Thus, a large, easily identified proportion of the follicles of the reconstituted bursas are populated by cells which cannot diversify Ig surface receptors produced from these overexpressed Ig transgenes.

Avian B-cells process and present of antigen in the context of the major histocompatibility complex (MHC). Thus, proteins expressed from viral vectors in bursal stem cells and their progeny are processed, and presented on the cell surface with MHC molecules. Presentation of antigen on B-cells early in the development of the immune system (equivalent to self-antigen) results in specific peripheral tolerance due to developmental deletion of reactive T-cells and either deleted or functionally defective B-cells (Fulcher et al., 1994). The fact that recipient birds are treated with cyclophosphamide to destroy endogenous bursal follicle populations, and are generally immunospressed as a consequence (Eskola et al., 1974), at a minimum delays if does not eliminate immune responses to neoantigens expressed on reconstituted syngeneic bursal cells. However, since some viral antigens given to late chick embryos have produced immune responses (Sharma et al., 1982), it is possible that a immune response will eventually occur resulting in antibodies and/or cytotoxic T-cell reactions against the bursal cells and peripheral B-cells expressing an antigenic transduced protein. The use of 15 day embryonic donors/recipients in primary transplants minimizes this possibility.

B. Ablation of Lymphoid Cells

The Bursa of Fabricus of host embryos is ablated in order to reconstitute it with transfected cells. Ablation of bursal cells may be carried out, for example, by the technique initially described by Eskola and Toivanen (1974). In brief, a small hole is cut in the egg shell of an approximateley 10–18 day old egg, preferably 15 days. The chorioallantoic vein is localized by transillumination and 0.10–0.15 ml of freshly prepared cyclophosphamide solution is injected into the vessel. The injection is repeated on three consecutive days. While this is a standard means of ablating lymphoid cells, modifications of this method and alternate means would be well within the purview of one of ordinary skill.

C. Bursal Stem Cell Transfection and Culture

Interruption of cell-cell contact within the normal follicular architecture initiates a very rapid apoptotic cell death response in all embryonic bursal lymphoblasts within a few hours, for example after dispersion of bursal follicle cells in short term culture (Neiman et al., 1991). However, short term culture of bursal stem cells in vitro is an essential requirement for introduction of gene transfer vectors. There is therefore a challenge to introduce the gene transfer vectors into the stem cells and reintroduce the transfected cells into the bursal environment before cell death occurs. Strategies to improve gene transfer into bursal stem cells include more rapid methods of introduction of vectors and methods of inhibiting apoptosis. The use of 15-day embryonic bursal cells mitigates these problems because these cells die much more slowly in culture than do cell from late stage bursal development.

1. Increasing the Concentration of Viral Vector Particles

Two different techniques are used to increase the proportion of successfully transduced bursal. The first is increase the concentration of viral vector particles to which each stem cell is exposed for a short time ex vivo before reinfusion into recipient birds. The short period (about 20 min) after dispersion of donor cells limits apoptosis. Retroviral particles attach to target cell receptors, are internalized and form preintegration complexes. Transit of this complex to the nucleus depends upon breakdown of the host nuclear envelope at mitosis (Roe et al., 1993; Lewis et al., 1994). Thus stem cells need to divide before degradation of the viral preintegration complex occurs in order to achieve integration of the vector and transgene into host DNA. Up to this point vector stocks utilized concentrations of infectious particles of $10^5$ to $10^6$/ml so that the effective m.o.i for transplanted stem cells ranged from 0.1 to 1.0. As described below technology now exists to increase the effective titers 10- to 100-fold which means as many as 10 viral vector particles could be conveniently introduced into each target stem cell prior to transplantation. This technique, in principle, should maximize the chances that stem cells arriving in depleted follicles will still contain effective vector preintegration complexes when they start to divide.

An alternate method to increase viral titer involves the co-cultivation of stem cells on vector producing cells. This facilitates an effective overall increase in viral titer.

2. Inhibition of Apoptosis

The second basic approach to optimization involves inhibiting cell death so that each stem cell can be transfected with an expression construct. In the context of using a retroviral vector, this facilitates the incubation for longer periods of time with vector producing cell lines. This increases the likelihood of infection and integration of the vector-transgene into host DNA. A variety of methods are well known within the art to inhibit or delay the onset of apoptosis. Apoptosis is regulatable at both the genetic and molecular level. Therefore, bursa may be transdused with an additional gene construct to inhibit apoptosis or apoptosis inhibitors may be provided to the relevant cells directly.

3. Combination Approaches

The two approaches described above are not, however, mutually exclusive. High titer infection (for example with an apoptosis inhibitor transducing vector) followed by co-cultivation with a helper cell line producing a viral vector-transgene of interest may be optimal for specific applications.

D. Expression Constructs

Expression of proteins in the context of the instant invention is facilitated by the transformation of bursal cells with specifically engineered nucleic acid constructs. Exemplary constructs useful for the transformation of bursal stem cells have been previously described. (See, U.S. Pat. Nos. 5,470,726 & 5,766,945, herein expressly incorporated by reference; Miller et al., 1991; ATCC CRL 10686). These constructs include the necessary sequence information to promote expression of the desired protein once properly integrated into a cell.

The term "expression vector and/or construct" means any type of genetic construct containing a nucleic acid coding for a gene product in which part and/or all of the nucleic acid encoding sequence is capable of being transcribed. The transcript may be translated into a protein, polypeptide and/or peptide but it need not be.

Particularly useful vectors are contemplated to be those vectors in which the coding portion of the DNA segment, whether encoding a full length protein, polypeptide and/or smaller peptide, is positioned under the transcriptional control of a promoter. A "promoter" refers to a DNA sequence recognized by the synthetic machinery of the cell, and/or introduced synthetic machinery, required to initiate the specific transcription of a gene. The phrases "operatively positioned", "under control" and/or "under transcriptional control" means that the promoter is in the correct location and/or orientation in relation to the nucleic acid to control RNA polymerase initiation and/or expression of the gene.

The promoter may be in the form of the promoter that is naturally associated with a gene, as may be obtained by isolating the 5' non-coding sequences located upstream of the coding segment and/or exon, for example, using recombinant cloning and/or PCR™ technology, in connection with the compositions disclosed herein (PCR™ technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, and/or heterologous promoter. As used herein, a recombinant and/or heterologous promoter is intended to refer to a promoter that is not normally associated with a gene in its natural environment. Such promoters may include promoters normally associated with other genes, and/or promoters isolated from any other bacterial, viral, eukaryotic, and/or mammalian cell, and/or promoters made by the hand of man that are not "naturally occurring," i.e., containing difference elements from different promoters, and/or mutations that increase, decrease, and/or alter expression.

Naturally, it will be important to employ a promoter that effectively directs the expression of the DNA segment in the cell type, organism, and/or even animal, chosen for expression. The use of promoter and/or cell type combinations for protein expression is generally known to those of skill in the art of molecular biology, for example, see Sambrook et al. (1989), incorporated herein by reference. The promoters employed may be constitutive, and/or inducible, and/or can be used under the appropriate conditions to direct high level expression of the introduced DNA segment, such as is advantageous in the large-scale production of recombinant proteins and/or peptides.

At least one module in a promoter generally functions to position the start site for RNA synthesis. The best known example of this is the TATA box, but in some promoters lacking a TATA box, such as the promoter for the mammalian terminal deoxynucleotidyl transferase gene and/or the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted and/or moved relative to one another. In the tk promoter, the spacing between promoter elements can be increased to 50 bp apart before activity begins to decline. Depending on the promoter, it appears that individual elements can function either co-operatively and/or independently to activate transcription.

The particular promoter that is employed to control the expression of a nucleic acid is not believed to be critical, so long as it is capable of expressing the nucleic acid in the targeted cell. Thus, where a chicken cell is targeted, it is preferable to position the nucleic acid coding region adjacent to and/or under the control of a promoter that is capable of being expressed in a chicken cell. Generally speaking, such a promoter might include either a chicken and/or viral promoter.

In various other embodiments the Rous sarcoma virus long terminal repeat, FAV major late promoter, MDV1 glycoprotein B (gB) promoter or other avian compatible promoter can be used to obtain high-level expression of the instant nucleic acids. The use of other viral and/or avian cellular and/or bacterial phage promoters which are well-known in the art to achieve expression are contemplated as well, provided that the levels of expression are sufficient for a given purpose.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one and/or more transcriptional proteins.

The basic distinction between enhancers and/or promoters is operational. An enhancer region as a whole must be able to stimulate transcription at a distance; this need not be true of a promoter region and/or its component elements. On the other hand, a promoter must have one and/or more elements that direct initiation of RNA synthesis at a particular site and/or in a particular orientation, whereas enhancers lack these specificities. Promoters and/or enhancers are often overlapping and/or contiguous, often seeming to have a very similar modular organization.

Additionally any promoter/enhancer combination (as per the Eukaryotic Promoter Data Base EPDB) could also be used to drive expression. Use of a T3, T7 and/or SP6 cytoplasmic expression system is another possible embodiment. Eukaryotic cells can support cytoplasmic transcription from certain bacterial promoters if the appropriate bacterial polymerase is provided, either as part of the delivery complex and/or as an additional genetic expression construct.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

1. Retroviral Systems

The exemplified retroviral system originally used to introduce v-myc into bursal follicles by the transplantation technique was a "recovered" avian myelocytomatosis virus called HB1(Neiman et al., 1985; Thompson et al., 1987; Enrietto et al., 1983). HB 1 is defective and requires a subgroup C helper-virus (tdB-77). Initially, simple infection by incubation of donor bursal cells for 30 minutes ex vivo with HB 1(tdB-77) stocks at multiplicity's of infection (m.o.i.) of about 1 infectious unit (I.U.)/cell yielded 5–20% TF in primary transplants, and as expected essentially 100% TF in secondary transplants. This degree of successful v-myc gene transfer could be improved in primary transplants by overnight co cultivation of embryonic bursal lymphoblasts on monolayers producing high titers (about $10^6$ I.U/ml) of HB1(tdB-77) yielded 20–60% TF in primary transplants (and, again, essentially 100% TF in secondary transplants).

HB1(tdB-77) is a spreading viral complex which causes a variety of lethal tumors in other organs (Enrietto et al., 1983), Therefore, analysis and utilization of recipient birds was quite limited. In order to avoid these problems, and make the system more useful, a helper-free vector, LXSN-HB1, was constructed in the vector system LXSN (Miller et al., 1989) to use for transducing the HB1 v-myc gene into bursal stem cells. This defective retroviral vector system is in widespred use including for clinical gene transfer/therapy experiments. Plasmid LXSN-HB1 was constructed and characterized as described in detail in Thompson et al. (1987), which is incorporated herein by reference in its entirety.

This vector, which drives transcription of the inserted HB1 v-myc gene from a murine leukemia virus-derived retroviral LTR, and transcription of a neomycin resistance gene, neo$^r$, from an internal SV-40 promoter, was expressed, as helper free virus, from the PG13 helper cell line as described (Miller et al., 1991 and U.S. Pat. No. 5,470,726). A clone producing virus with an infectious titer on HeLa cells of about $10^5$ I.U./ml was selected for further studies. As described in Thompson et al. (1987), successful transduction of high level v-Myc protein expression with the helper-free vector was demonstrated on a bursal cell line. Transplantation assays were then carried out following co-cultivation of embryonic bursal lymphoblasts on this PG-13 clonal cell line producing LXSN-HB1.

The proportion of TF among reconstituted follicles in primary transplants is no less than observed previously with HB1. Small lymphomas were observed in three of four bursas and metastatic lymphomas in the liver in two birds sacrificed 8 and 10 weeks after hatching. As also shown in Table 1, multiple secondary transplants were carried out with cells from the bursas of two of the primary transplants sacrificed about a month after hatching. The malignant potential of some of the TF cells in the primary transplants after only one month was demonstrated by the high proportion of intrabursal and hepatic lymphomas observed in the secondary transplants. Confirmation of the absence of infectious virus in these tissues was performed by plating up to $10^5$ TF cells on HeLa indicator cells. No G418 resistant colonies were obtained in this infectious center assay. Results demonstrate that neoplastic progression of v-myc-induced bursal stem cells occurred rapidly in the absence of spreading retroviral infection, presumably as an inevitable consequence of unregulated, high-level v-myc expression. Of principal significance for this application was the demonstration of effective myc gene transfer to bursal stem cells with a viral vector which infects target cells only once and does not spread and cause virus-related complications in the host.

The PG13 packaging line has been previously characterized (See U.S. Pat. No. 5,470,726, herein expressly incorporated by reference). The cell line is available from the ATCC, reference number CRL 10686. PG13 is a packaging line capable of using the Glvr-1 retroviral receptor for entry into cells. An alternative line that may be used is the PT67 cell line described in U.S. Pat. No. 5,766,945 (herein expressly incorporated by reference), which may use both the Glvr-1 or Ram-1 retroviral receptor on target cells for entry. The PG13 packaging lines are preferred in the context of the invention because they produce a higher vector titer and the viral particles are more effective in transducing target cells.

The LNCX vector has been previously described (Miller, et al. 1989). This expression system provides the vector backbone for the light chain fusion expression constructs. The LXCG expression construct which encodes green fluorescent protein incorporates a modified LXCN vector, which is in turn a derivative of LXSN (Miller, et al. 1989).

2. Other Gene Transfer Methods

In addition to the discussed retroviral system, suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, the DNA constructs of relevance to the instant invention may be introduced into organelle(s), cell(s), tissue(s) or organism(s) may be stably or transiently transformed.

3. Selection Systems

A number of selection systems may be used, including, but not limited to, the herpes simplex virus thymidine kinase (tk), hypoxanthine-guanine phosphoribosyltransferase (hgprt) and/or adenine phosphoribosyltransferase (aprt) genes, in tk$^-$, hgprt$^-$ and/or aprt$^-$ cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and/or hygromycin (hygro), that confers resistance to hygromycin.

E. Protein Production and Recovery

1. Protein Expression

Figure 2:
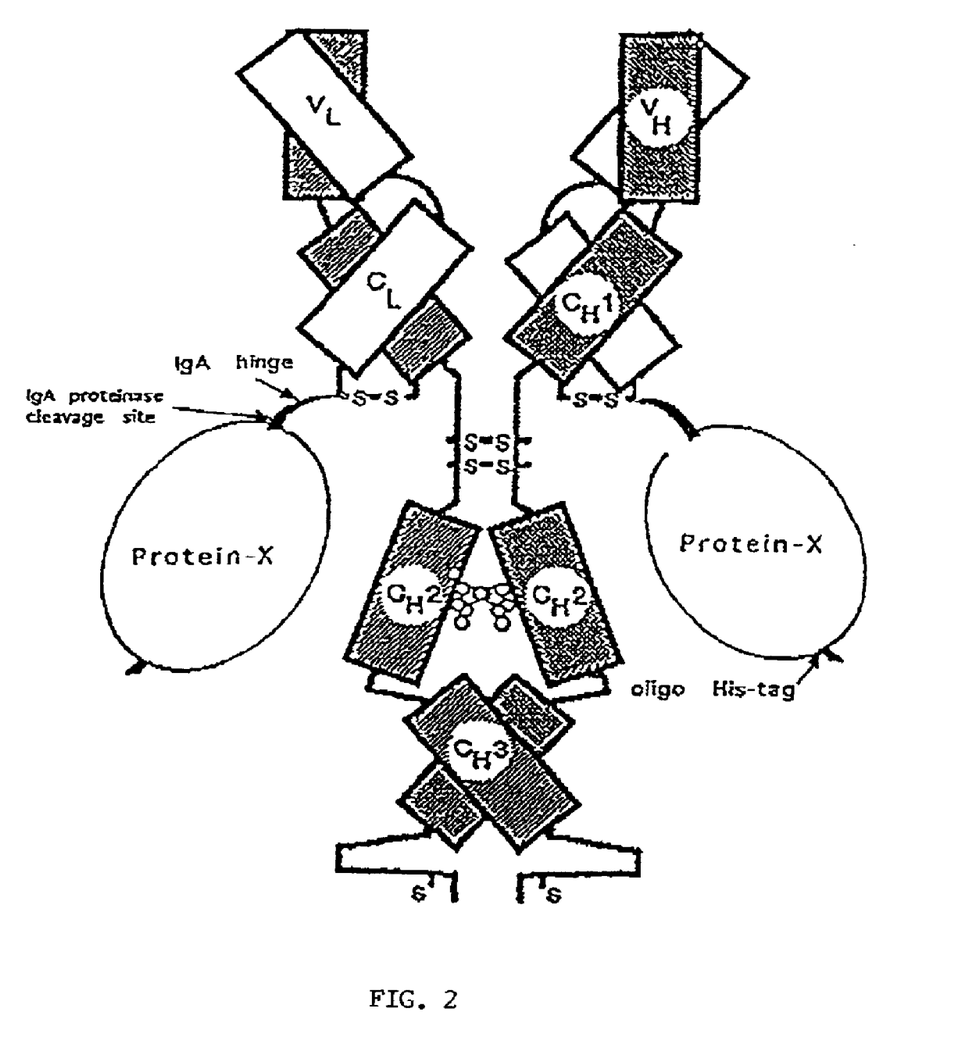
FIG. 2: Demonstrates an exemplary model of a fusion protein of the invention showing the fusion of the expressed protein to the C-terminus of the chicken light chain.
Figure 4:
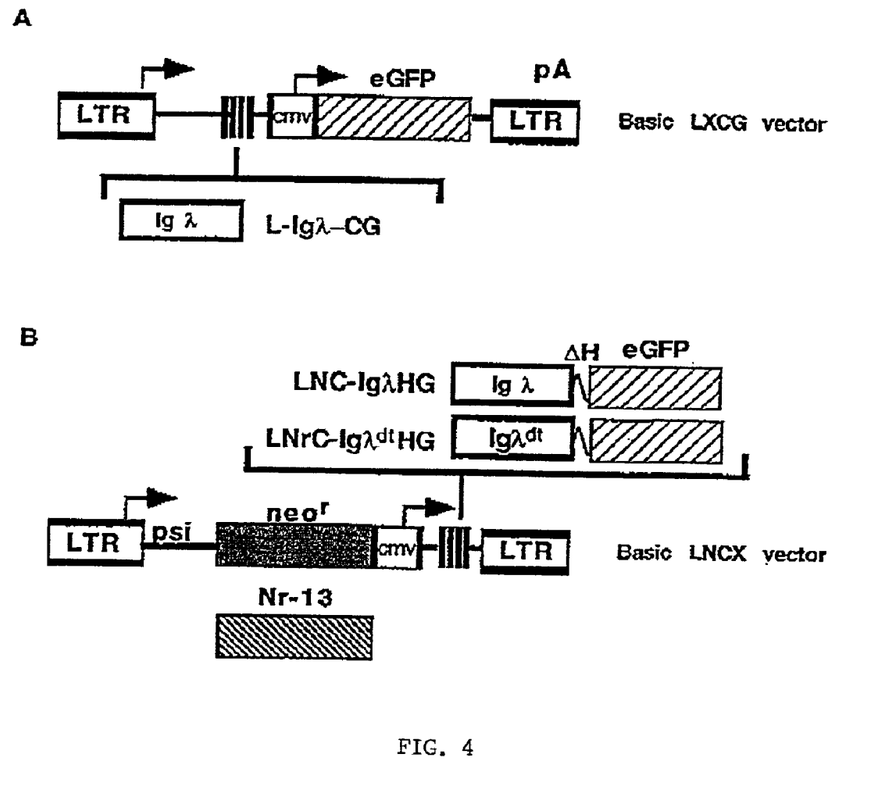
FIGS. 4A–B: Show exemplary LXCG-based vectors.

An exemplary model of the fusion protein is depicted in FIG. 2 and exemplary vector constructs are depicted in FIG. 4. As shown, the protein of interest X is expressed at the C-terminus of the chicken light chain. Based upon crystallographic data on immunoglobulin structure this region of the complete molecule is relatively unconstrained and fusions with a protein of interest does not interfere either with processing of light chain molecules mediated by signal sequences at the N-terminus or with hydrophobic pairing with endogenous heavy chains through V and C region domains. The addition of a spacer at the fusion site helps to minimize steric hindrance, for example with disulfide bonding of the C-terminus of light chains light with heavy chains. Proline rich hinge segment from human IgA are used for this purpose (Bachouchin et al., 1990) for two reasons: (Neiman et al, 1985) it is relatively protease resistant and should protect against adventitial cleavage; (Thompson et al., 1987) a commercially available (Boerhinger-Mannheim) highly specific IgA proteinase from *N. gonorrhea* cleaves efficiently at this site (Plaut et al., 1975). This property is useful for separation of protein X from the carrier Ig molecule. AC-terminal "oligoHis-tag" may also be included for rapid metal affinity column purification of protein X.

Constructs expressing these engineered light chain molecules are introduced into bursal stem cells using transplantation technology disclosed herein. Based on data from transgenic mice expressing Ig light chain transgenes, endogenous light chain production and/or incorporation into whole immunoglobulins in transduced bursal B-cells and their progeny is likely to be suppressed (Ritchie et al., 1984). Therefore, within stem cells and their progeny in the bursa and peripheral lymphoid tissues of recipient birds, these engineered light chains are seen to predominate, pair with appropriate endogenous heavy chains, be secreted into the circulation and, in mature hens, enter egg yolk in quantity. Purification of IgY by standard procedures recovers the whole engineered Ig fraction. By digesting with IgA proteinase followed by binding and elution from nickel affinity resins (e.g., commercially available from Novagen or Clontech) the polypeptide of interest is easily separated and purified from the whole IgY fraction by simple standard procedures. Variations on this theme with regard to tags and proteolytic cleavage sites can easily be envisioned to accommodate requirements associated with any particular protein. One complication could result if an antibody response occurred to the protein-X (see preceding section) and was present in significant amounts in the IgY fraction along with (and complexed to) the target protein. Depending upon the ratio of immune complex versus free protein it is envisioned that under some circumstances it might be necessary to include a preparative step(s) to dissociate the target protein and antibody.

2. Protein Purification

The present invention also provides purified, and/or in preferred embodiments, substantially purified, proteins, polypeptides, and/or peptides. The term "purified proteins, polypeptides, and/or peptides" as used herein, is intended to refer to an proteinaceous composition, isolatable from chicken cells or serum, wherein the protein, polypeptide, and/or peptide is purified to any degree relative to its naturally-obtainable state, i.e., relative to its purity within a cellular extract.

Proteins, peptides, or polypeptides expressed in the context of the instant invention may be full length proteins or they may be less then full-length proteins, such as individual domains, regions and/or even epitopic peptides.

Generally, "purified" will refer to a protein, polypeptide, and/or peptide composition that has been subjected to fractionation to remove various contaminants and which substantially retains activity.

Where the term "substantially purified" is used, this will refer to a composition in which the protein, polypeptide, and/or peptide forms the major component of the composition, such as constituting about 50% of the proteins in the composition and/or more. In preferred embodiments, a substantially purified protein will constitute more than 60%, 70%, 80%, 90%, 95%, 99% and/or even more of the proteins in the composition.

A peptide, polypeptide and/or protein that is "purified to homogeneity," as applied to the present invention, means that the peptide, polypeptide and/or protein has a level of purity where the peptide, polypeptide and/or protein is substantially free from other proteins and/or biological components. For example, a purified peptide, polypeptide and/or protein will often be sufficiently free of other protein components so that degradative sequencing may be performed successfully.

Various methods for quantifying the degree of purification of proteins, polypeptides, and/or peptides will be known to those of skill in the art in light of the present disclosure. These include, for example, determining the specific protein activity of a fraction, and/or assessing the number of polypeptides within a fraction by gel electrophoresis. Assessing the number of polypeptides within a fraction by SDS/PAGE analysis will often be preferred in the context of the present invention as this is straightforward.

To purify a protein, polypeptide, and/or peptide the composition comprising at least some proteins, polypeptides, and/or peptides will be subjected to fractionation to remove various contaminating components from the composition. In addition to those techniques described in detail herein below, various other techniques suitable for use in protein purification will be well known to those of skill in the art. These include, for example, precipitation with ammonium sulfate, PEG, antibodies and/or the like and/or by heat denaturation, followed by centrifugation; chromatography steps such as ion exchange, gel filtration, reverse phase, hydroxylapatite, lectin affinity and/or other affinity chromatography steps; Protein A; isoelectric focusing; gel electrophoresis; and/or combinations of such and/or other techniques.

It is specifically contemplated that proteins may be expressed with at least one fusion partner. In addition to fusing expressible proteins to chicken immunoglobulin, the protein may comprise an additional binding sequence to facilitate purification. Such purification methods are routine in the art. This is exemplified by the generation of an protein-HIS tag or protein-glutathione S-transferase fusion protein. Purification to homogeneity may be carried out with such fusion proteins using affinity chromatography such as, for example Ni-affinity chromatography or glutathione-agarose respectively.

Although preferred for use in certain embodiments, there is no general requirement that the expressed protein, polypeptide, and/or peptide always be provided in their most purified state. Indeed, it is contemplated that less substantially purified protein, polypeptide and/or peptide, which are nonetheless enriched, relative to the natural state, will have utility in certain embodiments.

Methods exhibiting a lower degree of relative purification may have advantages in total recovery of protein product, and/or in maintaining the activity of an expressed protein. Inactive products also have utility in certain embodiments, such as, e.g., in antibody generation.

3. Antibody Purification

Precipitation Methods. Precipitation is a fast way of concentrating proteins from a solution. The addition of highly charged ions such as ammonium and sulfate to a protein solution causes a disruption of the hydrogen bonds between the protein and water resulting in precipitation of proteins from the solution. Immunoglobulins (Ig) precipitate at low salt concentrations. An exemplary ammonium sulfate precipitation procedure is as follows:

1. Centrifuge the antiserum for 30 minutes at 3000×g to remove any debris.
2. Transfer the supernatant to a beaker, add a stir bar and place on a magnetic stirrer.
3. Add an equal volume of saturated ammonium sulfate solution to the stirring protein solution. Stir for 30–60 minutes at 2–6° C.
4. Centrifuge the mixture at 3000×g for 10–15 minutes.
5. Remove and discard the supernatant. Resuspend the pellet in PBS at 0.25 volumes of the starting volume.
6. Dialyze the solution against three changes of PBS overnight.
7. The dialyzed antibody solution may also contain some plasma proteins other than IgG from the serum. These contaminants can be diminished by repeating steps 3–5.

IgY purification Protocol. Methods for the purification of IgY from egg yolk are well known in the art, see for example, Polson, et al. 1985, Akita and Nakai, 1992 and U.S. Pat. Nos. 4,357,272, 4,550,019, 5,080,895, 5,420,253 and 5,367,054. In addition, kits are available from various commercial sources, i.e. Promega EggStract (Promega Corp., Madison Wis.). An exemplary technique is briefly summarized as follows: Egg yolk separated from the white, is washed with distilled water to remove as much albumen as possible and rolled on paper towels to remove adhering egg white. The membrane is punctured and the yolk allowed to flow into a graduated cylinder without the membrane. The egg yolk is then diluted in distilled water (acidified with 0.1 N HCl, predetermined to give the desired pH after dilution) and held for at least two hours before centrifugation (10,000×g for one hour at 4° C.) or filtration through Whatman No. 1 filter paper at 4° C. The resulting filtrate or water soluble fraction is further purified by salt precipitation, alcohol precipitation, ultrafiltration, gel filtration or anion exchange chromatography. Purity and recovery of immunoglobulin may be monitored at various stages by SDS-PAGE and/or radial immunodiffusion. The activity of the IgY can be evaluated by commonly employed immunodetection assays, such as, for example ELISA or Western blotting.

Antigen Columns. Antigen columns can provide the highest specificity in purifying antibodies specific for an antigen from the mixture of antibodies usually found in antisera. The antibodies purified by affinity purification of a polyclonal antiserum can have specificities approaching that of monoclonal antibodies, however, this technique requires high-affinity antibodies and large amounts of the antigen.

First, an antigen-column is prepared by covalently coupling the peptide antigen to a solid phase matrix by methods similar to the conjugation of a peptide to a carrier protein. The antiserum is then added. The specific antibodies bind to the antigen column and non-specific antibodies are washed away. Finally, the antibodies are eluted from the column by changing a parameter, e.g., lowering the pH to 2.8.

There are a variety of supports available for affinity chromatography. The types of supports can be divided into natural and synthetic matrices. Examples of natural matrices are agarose, cellulose, glass, silica, and alumina. Synthetic matrices include polyacrylamide, dextran, polystyrene, and microporous membranes.

When coupling the antigen to the solid support, recommendations similar to those for conjugating the antigen to a carrier protein apply. They include avoiding modification of the epitopes of the antigen and maintaining a natural orientation of the antigen.

Activation methods include cyanogen bromide, tresyl chloride, and N-hydroxysuccinimide. Pre-activated supports are available from a number of vendors including Pierce, Pharmacia, and Bio-Rad.

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

All of the specific experiments depend upon transduction of bursal stem cell with the retroviral vector, such as, for example LXCG. FIG. 4 depicts this basic vector.

Optimizing gene transfer to bursal stem cells. The generation of ultra high titer stocks of LXSN-AP (also referred to as LAPSN, described in Miller et al., 1994; which is incorporated herein by reference in its entirety) takes advantage of a vesicular stomatitis virus (VSV)-based pseudotyping strategy in which the envelope glycoprotein of VSV, VSV-G, is used to coat retroviral core particles containing LXSN genomes to produce high-titer, pantropic retroviral vectors. The various components of this technique have been described by several groups (Burns, et al. 1993, Yee, et al. 1994, Landau, et al. 1992). In brief, the production system is a cell line, 293T, which is exceptionally efficient for production of viral particles by transient transfection. The 293T cell are transfected, by calcium-mediated precipitation, with plasmid DNA containing LXSN-AP and DNA from three additional plasmids which produce the components of infectious particles: pVSV-G for the envelope, pJK3 encoding moloney leukemia virus gag and pol (capsid, matrix and reverse transcriptase) genes driven by an HIV-LTR promoter/enhancer, and pCMV-TAT providing high levels of TAT protein which is essential for the activity of the HIV LTR.

About 24 hours after transfection, host 293T cells begin to show cytotoxicity due to production of the VSV-G protein. Virus is then harvested from supernatants for the next 24 hours. The advantage of the VSV envelope, in addition to its very broad host range, is its exceptional resistance to inactivation. Therefore, unlike particles in retroviral envelopes, these VSV-G pseudotyped LXSN-AP viruses can be concentrated up to 100-fold by simple ultracentrifugation and resuspension of pelleted virus in small volumes (Burns, et al. 1993). Titers of resultant stocks are determined via the LXSN-AP neomycin resistance gene by induction of G418 resistant colonies on HeLa cells as described (Miller, et al. 1991, which is incorporated herein by reference in its entirety). Transient expression of VSV-G pseudotyped LXSN-AP yields titers of 106–107 I.U./ml from 293T-cells which rise to 108–109 I.U./ml in concentrated stocks. All procedures with these agents are conducted under FHCRC biosafety committee approved BL-2 conditions as prescribed by NIH guidelines VSV-G pseudotyped LXSN-AP stocks were tested (i.e., LXSN-AP(VSV-G)) by infection of several bursal derived cell lines available in the lab. Cells are pelleted, resuspended in concentrated virus at a multiplicity of infection (m.o.i.) of 5 to 10 for 20 min. at 37° C., washed and replated in culture. LXSN-AP(VSV-G) at high multiplicity is capable of rapidly infecting and expressing the indicator gene in chicken bursal cells.

The next step is to reconstitute bursal follicles with embryonic donor cells subjected to this high multiplicity infection procedure with LXSN-AP(VSV-G). The percentage of positive bursal follicles expressing the indicator AP transgene is scored by visual inspection. In addition, peripheral lymphoid tissue (spleen marrow and lymph nodes) is examined for the expression of the AP transgene using available antibodies to detect chicken Ig on the surface of B-cells, along with the AP enzymatic assay. This allows for the determination of the level of persistent transgene expression relative to the peripheral B-cell mass. Extinction of initially expressed transgenes in somatic stem cells has been an occasional issue in gene-transfer/therapy technology (Palmer, et al. 1991).

A series of LXSN based vectors which express genes which are strong and specific inhibitors of the cell death pathway in many systems function to overcome problems with apoptosis. These constructs, diagrammed in FIG. 3, express inhibitors of ICE-family cysteine proteases CRM-A from cowpox virus (Miura, et al. 1993) and p35 from baculovirus (Clem, et al. 1991) as well as Bcl-2 family members Bcl-2 (Korsmeyer, et al. 1993) and Bcl-X (Boise, et al. 1993). It is contemplated that such constructs will function in a similar manner to administration of phorbol dibutyrate. As mentioned above, the inventors were able to transiently protect dispersed embryonic bursal cell from dying by including phorbol dibutyrate (PDB) in the culture medium to allow time for viral integration and transgene expression.

To test the constructs containing putative apoptosis inhibitor vector, the vectors were used to infect cells. The infected cells were wash and then plated out onto PG13 packaging cell monolayers producing LXSN-AP (in the conventional retroviral envelope). Since no viral interference occurs under these conditions, stem cells protected by the first virus can be superinfected by cocultivation with the LXSN-AP producer PG13 cells for various lengths of time before transplantation. Analysis of reconstituted bursas for AP-expressing follicles are then compared to results with simple high titer infection with LXSN-AP(VSV-G) as described.

Figure 3:
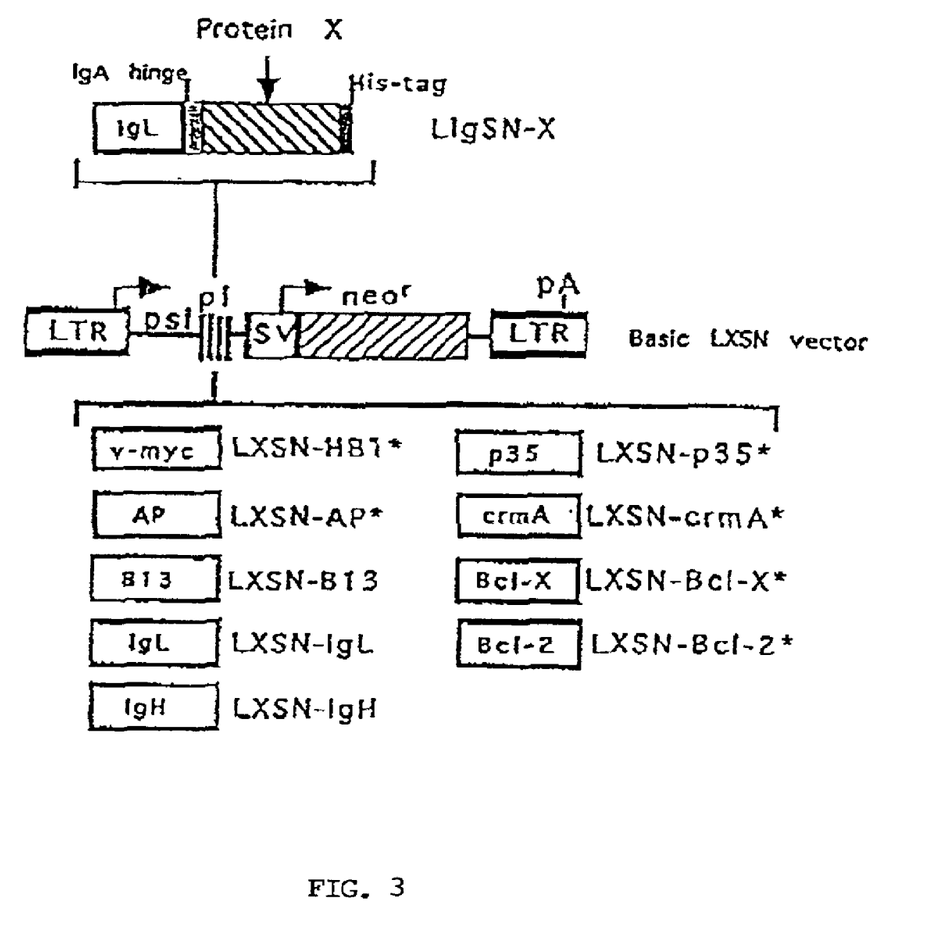
FIG. 3: Shows exemplary DNA constructs including the LIgSN-X vector, the basic LXSN vector and various cassettes useful for insertion as Protein X.

Expression of germ-line Ig on the surface of developing bursal lymphocytes. The cDNA clones for these studies are derived from embryonic bursal libraries previously prepared. Clones encoding the membrane bound forms of rearranged IgL and IgH germline forms (which together would encode surface IgM with germ-line V-regions) have been previously characterized (Thompson et al. 1987). FIG. 3 sets forth an exemplary method for inserting the Ig cDNAs into LXSN to prepare LXSN-IgH and -IgL. The vector for each or both of these transgenes is then used to transfect embryonic bursal stem cells by the strategy previously discussed. Transformed embryonic bursal stem cells are then used to reconstitute ablated bursal follicles. The single IgL and IgH germline transductions produce molecules which heterodimerize with the appropriate endogenous heavy or light chain molecule whose V-region has undergone physiologic V-region gene conversion producing hemi-diversified molecules on the surface of a large portion of the developing B-cell population. Transducing and expressing both IgL and IgH germ-line transgenes facilitates presention of IgM in permanently undiversified form on the surface of most or all developing bursal cells in reconstituted birds.

Multiple gene transductions. Double Ig-gene transductions are accomplished by simple variation of the basic experimental strategy. For production of high titer VSV-G pseudotyped vectors the neo$^r$ gene in LXSN is not required. Therefore one of the germ-line Ig transgenes can be inserted in place of neo$^r$. High multiplicity infection with VSV-G pseudotyped vectors achieves efficient gene transfer of bursal stem cells, with occupancy of the LTR driven site in LXSN by the second Ig transgene providing the needed two gene transduction system. Where inhibition of apoptosis or co-cultivation are required or desirable, then the apoptosis inhibitor gene is paired with one of the Ig germ-line genes in the VSV-G pseudotyped LXSN vector, and the second Ig transgene is transduced in the LXSN vector produced by the PG-13 helper cells. In addition to selectable neo$^r$ gene, this second strategy provides a three-gene transduction system; in this case two Ig genes and an apoptosis inhibitor gene.

Simple restriction endonuclease digestion and Southern blot hybridization analysis of sequences in germ-line light and heavy chain functional V-regions facilitates the detection and quantitation of the presence and persistence of V-region germ line alleles in the whole population of reconstituted bursal follicles. As described above (a) surface immunoglobulin with germ-line V-regions are critically involved in signaling proliferation of bursal lymphocytes, and (b) diversification of V-region domains is involved in signals for cell death and/or migration from bursa to peripheral lymphoid organs. Bursal follicles and peripheral lymphoid tissues are occupied by B-cells expressing surface Ig with hemi or completely undiversified V-regions at times in development when, normally, there are relatively few such cells.

Expression and isolation of large quantities of proteins. For purposes of demonstrating the expression and isolation of large quantities of useful protein in the chicken a specific humanized light chain antibody was chosen. Humanized antibodies are human Ig molecules in which antigen binding sites have been replaced by high affinity V-region specific antigen-binding sequences from murine monoclonal antibodies. The goal is to make clinically useful antibodies which do not stimulate major immune responses, as do complete mouse antibodies, when administered to humans. A principal barrier to his application is to learn how to graft mouse antigen binding pockets into the human V-region framework without significantly altering the ability of the engineered antibody effectively to bind the target antigen. Although some useful humanized antibodies have been produced by (Jones, et al. 1986) this engineering problem remains a significant obstacle (Foote, et al. 1992). αCD4 was selected for experimentation. This cloned human K light chain gene carries an engineered V-region of murine origin in which an original specificity for lysozyme (Jones, et al. 1986) has been replaced with specificity for the 120K envelope glycoprotein of human immunodeficiency virus (HIV). In addition to its specificity, αCD4 is important as a model humanized antibody because there is a great deal of structural data on which to base analysis and better refine principles for the construction of humanized antibodies. The viral vector created for this purpose designated LIgSN-αCD4 is diagrammed in FIG. 3 (where αCD4 is be substituted for -X in the diagram).

One advantage of the chicken IgY system is potential physiological glycosylation and other modification of produced proteins. Ectopic glycosylation sites in Ig V-regions are known to become physiologically glycosylated in vivo. The αCD4 construct includes such an ectopic glycosylation site.

The two gene transfer system described may be further modified such that both the engineered light and heavy chains would be introduced on carrier chicken IgL molecules. After cleavage by IgA proteinase in the IgY fraction the light and heavy chains reassemble to form a complete antibody.

Example 2

Development of the B-cell lineage in the bursa of Fabricius of chickens involves migration of precursors to the bursal anlage between day 10 and 14 of embryogenesis (LeDourain). Cells from this population with rearranged immunoglobulin (Ig) genes enter developing follicles about day 15, proliferate and undergo V-region diversification of their immunoglobulin genes by a gene conversion mechanism (Weill, et al. 1986, Thompson, c, McCormick, et al. 1989). Stem cell function, demonstrated in bursal transplantation experiments, persists in a small population of embryonic bursal cells which appear to be eliminated after hatching (Pink et al. 1987). The inventors have used these stem cells, from bursa between E18 and few days after hatching as targets of retroviral gene transfer and transplantation in studies of myc oncogene over expression (Neiman, et al. 1985, Thompson, et al. 1987) and of constitutive expression of the anti-apoptotic protein Nr-13 (Lee). Chick embryos in that interval of development can mount immune responses to histocompatability antigens (Longenecker, et al. 1982), and these successful transplantation experiments were carried out between inbred birds bearing the same histocompatibility alleles. Moreover the inventors have, here-to-fore with this technique, not achieved extensive gene transfer in studies with genes that do not confer a growth or survival advantage.

To extend the usefulness of this approach, the inventors have characterized cells of early bursal anlage for their ability to repopulate cyclophosphamide-ablated bursal follicles, and act as targets for retroviral gene transfer and expression of transgenes in the reconstituted B-cell lineage. The inventors found that bursal anlage between day 13 and 15 were rich in cells displaying early bursal markers. Day 15 embryonic bursal cells were relatively resistant to apoptosis induced by dispersion in short term culture and efficiently repopulated ablated follicles even in outbred day 15 recipients. Transduction of these cells with retroviral vectors expressing a green fluorescence protein (GFP) marker before transplantation produced GFP expression in about half as many reconstituted bursal cells in transplantation studies as the same vector achieved in a cultured B-cell line. This result was not affected by inclusion of an Igλ transgene in the vector. Vectors were then tested which expressed Igλ fused to GFP by a cleavable peptide hinge. The inventors found that surface expression and secretion of these molecules was influenced by V-region diversification. In gene transfer studies, the inventors detected these Ig-GFP fusion proteins in egg yolk from transplanted birds suggesting the potential use of this system for delivery in quantity of proteins of choice into eggs by engineered Ig carrier molecules.

Cells bearing early bursal antigens are abundant in day 14 and 15 bursal analage and are relatively resistant to dispersion-induced apotosis. The abundance of cells expressing early bursal markers was assessed by immunofluorescence. The monoclonal antibody Hy 86b5 recognizes 85–97% of both hematopoietic cells in embryonic day 10 yolk sack and leukocytes of marrow and peripheral blood of hatched chickens (Ewert). Consistent with previous flow cytometry analyses (Ewart), Hy 86b5 positive cells were abundant in day E14 and E15 bursal anlage and could be seen associating with epthelial buds of developing follicles. Sialyl Lewis is a carbohydrate epitope detected on the surface of embryonic bursal cells at and before day E15 (Thompson, et al. 1987) by flow cytometry and immunocytochemistry. An abundance of sialyl Lewis positive cells were seen by immunofluroescence. Double immunofluorescence analysis demonstrated extensive co-expression of both epitopes in this cell population. Ig gene rearrangement has been demonstrated in bursal anlage before embryonic day 15 (McCormack et al. 1989, Toivanen, et al. 1973) and expression of surface Ig (sI+) has been described in early bursal populations (Cooper, et al. 1960). Igλ was detected by immunofluorescence in day 15 bursa. The Igλ+ population appeared much smaller than that expressing the other two early antigens, and was associated principally with epithelial buds.

After embryonic day 15 almost all of the lymphoid population of the bursa is contained within rapidly growing bursal follicles (Le Dourain), become sIg+ (Thompson, et al. 1987) and show progressive loss of early markers such as sialyl Lewis (Thompson, et al. 1987) and Hy 86b5 (Ewart). Previously employed transplantation techniques utilized embryonic day 18 donor bursal cell suspensions which undergo rapid apoptotic cell death when dispersed in short term culture for co-cultivation with viral vector producing monolayers (Neiman, et al. 1985). Compared to cells from E18 bursal follicles, migrating day 15 bursal cells were relatively resistant to dispersion-induced apoptosis suggesting that the capacity for rapid induction of bursal apoptosis is installed after day 15 of embryogenesis. Furthermore, the relatively longer survival of embryonic day 15 cells in culture could assist in gene transfer by co-cultivation on viral vector-producing monolayers.

Reconstitution of cyclophosphamide-ablated bursas with embryonic day 15 bursal donor cells. The inventors tested the comparative ability of stem cell preparations from day 15 and day 18 embryos to reconstitute cyclophosphamide-ablated bursas. Donor cells from 15 day embryos were as efficient as those from day 18 embryos in reconstituting both day 15 and day 18 in bred, histocompatible SC recipients.

Retroviral gene transfer and expression of GFP and Igλ transgenes in a B-cell line and in reconstituted bursas. The inventors next tested the ability to carry out gene transfer into day 15 embryonic bursal stem cells using retroviral vectors. The initial studies were carried out with LXCG-based vectors, shown in FIG. 4A which expressed a GFP marker alone from the basic vector or an Igλ with a germline V region in addition to the GFP marker, LigλCG. Ample expression of the Igλ transgene was demonstrated in vector producing PG-13 packaging cell by western immunoblotting. Day 15 embryonic bursal cells were infected with these vectors by co-cultivation for 16 hr on virus-producing packaging cells, and GFP expression was assessed by flow cytometry 4 wk after reconstitution with these infected cells. In a study measuring the proportion of GFP positive cells in reconstituted bursas and compares these results with transduction of a B-cell line, DT-40, infected with these vectors in the same manner. In repeat studies, the inventors achieved from 9 to 12% expression of GFP in DT-40 cells, over a wide range of intensity, with either vector. In reconstituted bursas the inventors achieved from 4.5 to 7.2% GFP positive populations without obvious differences in results between vectors. The inventors concluded that the inventors could achieve retroviral gene transfer and expression of GFP in reconstituted bursas using day 15 embryonic donor cells, albeit at about half of the efficiency of transduction achieved in a B-cell line in culture.

Construction and expression of modular vectors expressing Igλ molecules fused to GFP by a C-terminal cleavable peptide hinge. Although germ line Igλ was expressed in packaging cells the inventors could not evaluate the expression of the germ line Igλ transgene from LIgλCG in the bursal transplantion studies because of endogenous Igλ (and the lack of specific anti-idiotype antibodies). To address this problem, and to analyze Ig light chains expressed from transgenes in this system, the inventors prepared and characterized viral vectors expressing Igλ fused to GFP (FIG. 4B).

Example 3

The HB1 v-myc transgene confers a strong growth phenotype in TF cells which give them a strong growth advantage over normal stem cells and their progeny. Therefore, a first step in testing the general applicability of this approach was to determine whether a growth-neutral gene could be transferred and expressed efficiently in reconstituted follicles. For this purpose a heat stable human placental alkaline phosphatase(AP) gene was inserted into the LXSN vector to produce LXSN-AP. The construct was produced in high titer (about $10^6$ I.U/ml) from the PG13 helper cell system. Cells and tissues successfully transduced with this viral construct can easily be scored by heating paraformaldehyde fixed sections, or cytofuged cell populations on slides, to inactivate any endogenous AP activity. The heat resistant enzymatic gene product of LXSN-AP is then detected by incubation with substrate and indicator (X-phos and nitro-blue tetrazolium). Reconstituted bursal follicles were successfully transduced with LXSN-AP four weeks after transplantation and hatching.

The proportion of AP expressing follicles was about 20–30%, and, therefore, somewhat lower than achieved with v-Myc tranduced with LXSN-HB1. This difference potentially reflects the strong growth advantage conferred on bursal lymphoblasts by overexpression of v-Myc. Nevertheless this is an impressive level of expression for an unselected transgene.

Example 4

This example shows the construction of a transducing virus for transduction of IgL-GFP fusion proteins. Within this example, the fusion proteins were composed, from N to C termini, of (1) the diversified light chain immunoglobulin, $Ig\lambda^{dt}$, cloned in this laboratory from the DT-40 cell line, a B-cell line derived from the chicken bursa of Fabricius, (2) a Hinge, based on the hinge region of murine IgA with the amino acid sequence SSPVPSTPPTPSPSTPPTPSPSLE (SEQ ID NO. 1) and (3) enhanced Green Fluorescent Protein (eGFP, Clontech Corp., Palo Alto, Calif.). The DNA encoding each of the fusion protein elements generated by polymerase chain reactions (PCR) using primers of 28 nucleotides including a restriction endonuclease recognition site in positions 4 to 10. The $Ig\lambda^{dt}$ the template DNA was amplified from the original clone in plasmid pCR 2.1 (Invitrogen., Carlsbad, Calif.) using the 5' PCR primer containing a Hind III site was GCTAAGCTTCCGCCATG-GCCTGGGCTC (SEQ ID NO: 2), and the 3' PCR primer containing an Xba I site was GGCTCTAGAGCACTCG-GACCTCTTAGG (SEQ ID NO: 3). The Hinge template DNA sequence (SEQ ID NO: 4: CCT GTG CCA TCC ACA CCT CCA ACA CCT AGC CCA TCC ACA CCT CCA ACA CCT AGC CCA AGC) encoding the Hinge was synthesized on an Applied Biosystems Inc. DNA synthesizer (Applied Biosystems, Inc., Foster City, Calif.). The DNA fragment encoding the Hinge regions was amplified from the template using the 5' PCR primer containing an Xba I site (SEQ ID NO: 5: GGCTCTAGA CCTGTGCCATCCACA) and the 3' PCR primer containing an Xho I site (SEQ ID NO: 6: GCCCTCGAGGCTTG GGCTTGGGCTAGGTGT). The eGFP the template DNA was the GFP transducing retroviral construct LNCG. The plasmid pLNCG is derived from plasmid pLNCX (Miller and Rosman, 1989; which is incorporated herein by reference in its entirety) in which a cDNA encoding eGFP is inserted into the polylinker site between the CMV promoter and the LTR. The eGFP cDNA was amplified from pLNCG using the 5' PCR primer containing an Xho I site (SEQ ID NO: 7: GGACTCGAGATGGTGAG-CAA GGAG) and the 3' GFP primer containing a Hpa I site (SEQ ID NO: 8: GCAGGTAACTTACTTGTACAGCTCCTC). Each PCR product was cloned separately into the TA cloning site of plasmid pCR 2.1 (Invitrogen), and the resulting plasmids were named: pCR-Igldt, pCR-H, pCR-GFP respectively. Each plasmid was sequenced to rule out PCR introduced sequence errors.

The PCR product inserts in each of the plasmids described above were excised by digestion with restriction endonucleases at the unique sites in the 5' and 3' primers as follows: pCR- $Ig\lambda^{dt}$ with Hind III and Xba-I, pCR-H with Xba-1 and Xho-I, and pCR-GFP with Xho and Hpa-I. These fragments were then cloned sequentially in the compatible restriction sites of the polycloning site of pGEMllzf (Promega, Madison, Wis.) to produce p $Ig\lambda^{dt}$ HG. The junctions of the elements were sequenced again to document joints in the correct reading frame for protein translation.

The basic retroviral vector was LNCX (Miller and Rosman, 1989) was prepared by digestion with Hind III and Hpa I to linearize the vector. The fusion protein encoded by the insert was prepared from p $Ig\lambda^{dt}$ HG first by cutting at the Eco R1 site of the residual polylinker site near the 3' end of the insert. The recessed 3' ends of each cut were filled in with Klenow DNA polymerase to produce a blunt end, and the whole insert released by cutting at the 5' end with Hind III. The insert was then cloned by ligation into the prepared viral vector.

The Nr-13 clone (Lee et al., 1999; Germain Gillet, CNRS, ENS Lyon, France) as a cDNA insert in pBluescript (Stratagene, La Jolla, Calif.). The Nr-13 coding sequence was excised from this plasmid by cutting with Eco RV and Bam H1. Viral vector DNA containing the fusion protein sequence was prepared by first cutting with Bcl-1 and blunt ends generated as described above. The vector was then cut at the unique Bam H1 site, removing the $Neo^r$ gene, and the Nr-13 fragment ligated in its place to produce the vector LNrC-$Ig\lambda^{dt}$ HG.

DNA from NrC-$Ig\lambda^{dt}$ HG was introduced by transient transfection into the viral packaging line BOSC-23. At 48 hours after transfection supernatants were harvested and used to infect the packaging line PG-13, which results in viral particles with a Gibbon Ape Leukemia Virus (GALV) envelope, which efficiently infect chicken bursal cells. Individual PG-13 clones were inspected by immunofluorescence for GFP expression from the viral vector. Promising clones were co-cultivated with DT-40 cells overnight and the DT-40 assessed for transduction by GFP fluorescence. Virus producing PG-13 clones, which gave 10–60% GFP positive DT-40 cells after overnight co-cultivation, were stored in liquid nitrogen for future use. These clones were co-cultivated with embryonic bursal stem cell preparations used for transplantation experiments as generally described above.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Akita et al., *J. Food Sci.* 57, 629, 1992.
Asakawa et al., *Cell. Immunol.* 147, 180–187, 1993.
Baba et al., *Proc. Nat'l Acad. Sci. USA* 82, 213–216, 1985.
Bachouchin et al., *J. Biol. Chem.* 265, 3738–3743, 1990.
Boise et al., *Cell* 74, 597–608, 1993.
Burns et al., *Proc. Nat'l Acad. Sci. USA* 90, 8033–8037, 1993.
Buxton, *J. Gen. Microbiol.* 7, 268, 1952.
Chen and Okayama, *Mol. Cell. Biol.* 7, 2745–2752, 1987.
Clem et al., *Science* 254, 1388–1390, 1991.
Cooper et al., *J. Nat'l Cancer Inst.* 41, 373–389, 1960.
Enrietto et al., *Cell* 35, 369–379, 1983.
Eskola et al., *Cell. Immunol.* 13, 459–471, 1974.
Fechheimer et al., *Proc. Nat'l Acad. Sci. USA* 84, 8463–8467, 1987.
Foote et al., *J. Mol. Biol.* 224, 487–499, 1992.
Fraley et al., *Proc. Nat'l. Acad. Sci. USA* 76, 3348–3352, 1979.
Fulcher et al., *Autoimmunity* 19, 135–140, 1994.
Fulton et al., *Eur. J. Immunol.* 25, 2069–2076, 1995.
Gavrielli et al., *J. Cell Biol.* 119, 493–501, 1992.
Goodnow et al., *Cold Spring Harbor Symposium on Quantitative Biology* 54, 907–920, 1989.
Hayward et al., *Nature* 290, 475–480, 1981.
Gopal, *Mol Cell. Biol.,* 5, 1188–1190, 1985.
Graham and Van Der Eb, *Virology* 52, 456–467, 1973.
Harland and Weintraub, *J. Cell Biol.* 101, 1094–1099, 1985.
Harlow, E. and Lane, D., 1988. Antibodies: A Laboratory Manual, Cold Spring Harbor Press.
Jalkanen et al., *Nature* 311, 69–71, 1984.
Jones et al., *Nature* 321, 522–525, 1986.
Kaeppler et al., *Theor. Appl. Genet.,* 84, 560–566, 1992.
Kaneda et al., 1989
Kato et al., *J. Biol. Chem.* 266, 3361–3364, 1991.
Korsmeyer et al., *Seminars in Cancer Biology* 4, 327–332, 1993.
Landau et al., *J. Virol.* 66, 5110–5113, 1992.
Lee et al., *Genes & Development* 13, 718–28, 1999
Lewis et al., *J. Virol.* 68, 510–516, 1994.
Longenecker et al., *Surv. Immunol. Res.* 1, 205–11, 1982.
McCormack et al., *Genes and Development* 3, 838–847, 1989.
Miller et al., *Proc. Nat'l Acad. Sci. USA* 91, 78–82, 1994
Miller and Rosman, *BioTechniques* 7, 980–990, 1989
Miller et al., *J. Virol.* 65, 2220–2224, 1991.
Miura et al., *Cell* 75, 653–660, 1993.
Motyka et al., *Eur. J. Immunol.* 21, 1951–1958, 1991.
Neiman et al., Malignant Lymphoma of the Bursa of Fabricius: Analysis of Early Transformation. In: Cold Spring Harbor Conferences on Cell Proliferation. Viruses in Naturally Occurring Cancer. Vol. 7. (Eds: Essex et al.,) Cold Spring Harbor Laboratory, Cold Spring Harbor, N.Y., 519–528, 1980.
Neiman et al., *Proc. Nat'l Acad. Sci. USA* 82, 222–236, 1987.
Neiman et al., *Proc. Nat'l Acad. Sci. USA* 88, 5857–5861, 1991.
Nicolau and Sene, *Biochem. Biophys. Acta,* 721:185–190, 1982.
Nicolau et al., 149, 157–176, 1987.
Omirulleh et al., *Plant Mol. Biol.,* 21, 415–28, 1993.
Palmer et al., *Proc. Nat'l Acad. Sci USA* 88, 1330–1334, 1991.
Pink, J R, *Immunol Rev.* 91, 115–28, 1986.
Plaut et al., *Science* 190, 1103–1105, 1975.
Potrykus et al., *Mol. Gen. Genet.* 199, 183–188, 1985.
Reynaud et al., *Cell* 40, 283–291, 1985.
Reynaud et al., *Cell* 59, 171–183, 1989.
Rippe et al., *Mol. Cell Biol.,* 10, 689–695, 1990.
Ritchie et al., *Nature* 312, 517–521, 1984.
Roe et al., *EMBO J.* 12, 2099–2108, 1993.
Sharma et al., *Avian Dis.* 26, 860–870, 1982.
Svendesen et al., *Lab. Animal Sci.* 45, 89–93, 1995.
Thompson et al., *Cell* 51, 371–381, 1985.
Thompson et al., *Cell* 48, 369–378, 1987.
Thacker et al., *J. Virol.* 69, 6439–6444, 1995.
Toivanen et al., *Eur. J. Immunol.* 3, 585–595, 1973.
Weill et al., *Science* 238, 1094–98, 1986.
Weill et al., *Proc. Nat'l Acad. Sci. USA* 83, 3336–3340, 1986.
Wong et al., *Gene,* 10, 87–94, 1980.
Yee et al., *Proc. Nat'l Acad. Sci. USA* 91, 9564–9568, 1994.
Yom et al., *Amer. J. Clin. Nutr.* 58(suppl), 299S–306S, 1993.
WO 94/09699
WO 95/06128
U.S. Pat. No. 5,384,253
U.S. Pat. No. 5,789,215
U.S. Pat. No. 5,994,624
U.S. Pat. No. 5,981,274
U.S. Pat. No. 5,945,100
U.S. Pat. No. 5,780,448
U.S. Pat. No. 5,736,524
U.S. Pat. No. 5,702,932
U.S. Pat. No. 5,656,610
U.S. Pat. No. 5,589,466
U.S. Pat. No. 5,580,859
U.S. Pat. No. 5,610,042
U.S. Pat. No. 5,322,783
U.S. Pat. No. 5,563,055
U.S. Pat. No. 5,550,318
U.S. Pat. No. 5,538,877
U.S. Pat. No. 5,538,880
U.S. Pat. No. 5,302,523
U.S. Pat. No. 5,464,765
U.S. Pat. No. 5,591,616
U.S. Pat. No. 5,563,055
U.S. Pat. No. 4,684,611
U.S. Pat. No. 4,952,500

What is claimed is:

1. A method for producing a selected polypeptide comprising in an avian host:
   (a) ablating lymphoid cells in a first avian host embryo;
   (b) infusing into said embryo bursal stem cells from a donor, wherein said bursal stem cells have been infected with a transducing virus that contains a nucleic acid encoding said selected polypeptide;
   (c) obtaining bursal follicle from said first avian host after hatching; and
   (d) repopulating a second avian host embryo with said bursal follicle cells obtained in part (c), wherein lymphoid cells of the second avian host have been ablated, whereby said bursal follicle cells of said first avian host produce said selected polypeptide.

2. The method of claim 1, wherein ablation is achieved by treatment of said first avian host embryo with radiation or an alkylating agent.

3. The method of claim 1, wherein said first or second avian host is a chicken.

4. The method of claim 1, wherein the transducing virus is a retrovirus.

5. The method of claim 1, wherein the transducing virus further encodes an anti-apoptotic factor.

6. The method of claim 5, wherein the anti-apoptotic factor is NR-13.

7. The method of claim 1, wherein the selected polypeptide is an immunomodulator, a hormone, an enzyme, an antibody, a cell signaling molecule, a DNA binding protein or a protein inhibitor.

8. The method of claim 1, wherein said nucleic acid encoding said selected polypeptide is fused to a nucleic acid encoding an immunoglobulin light chain.

9. The method of claim 8, wherein the fusion between the selected polypeptide and immunoglobulin light chain encoding nucleic acids is through a nucleic acid encoding a cleavable peptide.

10. The method of claim 9, wherein said cleavable peptide sequence is an IgA hinge region.

11. The method of claim 9, further comprising the step of cleaving said cleavable peptide sequence.

12. The method of claim 8, further comprising the step of isolating said selected polypeptide.

13. The method of claim 12, wherein said selected polypeptide is isolated from an egg yolk.

14. The method of claim 12, wherein said selected polypeptide is purified using ammonium sulfate precipitation.

15. The method of claim 13, wherein said selected polypeptide purified 100-fold over the starting material.

16. The method of claim 13, wherein said selected polypeptide is purified.

17. The method of claim 13, wherein said selected polypeptide is purified to 95% purity.

18. The method of claim 1, wherein said first avian host embryo is 15 days old.

19. The method of claim 1, wherein said embryonic bursal stem cells are from a 15 day old embryo.

20. The method of claim 1, wherein said first avian host embryo and said embryonic bursal stem cells are syngeneic.

21. A method of repopulating an avian host with transduced bursal cells comprising:
   (a) providing an avian stem cell, wherein said burasal stem cell is syngeneic to a first avian host;
   (b) transducing said bursal stem cell with a first transducing virus that contains a nucleic acid encoding an apoptosis inhibitor;
   (c) infusing said first avian host with the transduced bursal stem cell;
   (d) obtaining bursal follicle cells from said first avian host after hatching; and
   (e) repopulating a second avian host embryo with said bursal follicle cells obtained in part (d), wherein lymphoid cells of the second avian host habe been ablated.

22. The method of claim 21, further comprising transducing said bursal stem cell at a multiplicity of infection of greater than 1.

23. The method of claim 21, wherein said first or second avian host is a chicken.

24. The method of claim 21, wherein said bursal stem cell also is transduced with a second transducing virus containing a nucleic acid encoding a select polypeptide.

25. The method of claim 24, wherein said selected polypeptide is an immunomodulator, a hormone, an enzyme, an antibody, a cell surface molecule, a DNA binding protein or a protein inhibitors.

26. The method of claim 21, wherein the first transducing virus is a retrovirus.

27. The method of claim 21, wherein said first avain host is an embryo, lymphoid cells of which have been ablated.

* * * * *

UNITED STATES PATENT AND TRADEMARK OFFICE
CERTIFICATE OF CORRECTION

PATENT NO. : 6,946,266 B2
DATED : September 20, 2005
INVENTOR(S) : Neiman It is certified that error appears in the above-identified patent and that said Letters Patent is hereby corrected as shown below:

Column 28,
Line 37, delete "stem cell" and insert -- bursal stem cell --.
Line 37, delete "burasal" and insert -- bursal --.
Line 49, delete "habe" and insert -- have --.
Line 57, delete "select" and insert -- selected --.
Line 64, delete "avain" and insert -- avian --.

Signed and Sealed this

Thirtieth Day of May, 2006

JON W. DUDAS
*Director of the United States Patent and Trademark Office*

SEQUENCE LISTING

<160> NUMBER OF SEQ ID NOS: 8

<210> SEQ ID NO 1
<211> LENGTH: 24
<212> TYPE: PRT
<213> ORGANISM: chicken

```
<400> SEQUENCE: 1

Ser Ser Pro Val Pro Ser Thr Pro Pro Thr Pro Ser Pro Ser Thr Pro
 1               5                  10                  15

Pro Thr Pro Ser Pro Ser Leu Glu
            20

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
gctaagcttc cgccatggcc tgggctc                                       27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
ggctctagag cactcggacc tcttagg                                       27

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
cctgtgccat ccacacctcc aacacctagc ccatccacac ctccaacacc tagcccaagc   60

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
ggctctagac ctgtgccatc caca                                          24

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
gccctcgagg cttgggcttg ggctaggtgt                                    30

<210> SEQ ID NO 7
<211> LENGTH: 24
<212> TYPE: DNA
<213> ORGANISM: Artificial Sequence
```

-continued

```
<220> FEATURE:
<223> OTHER INFORMATION: Description of Artificial Sequence:  Synthetic
      Primer

<400> SEQUENCE: 7
ggactcgaga tggtgagcaa ggag                                             24

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 8
gcaggtaact tacttgtaca gctcctc                                          27
```